United States Patent
Stienstra

(10) Patent No.: US 6,833,236 B1
(45) Date of Patent: Dec. 21, 2004

(54) PLATELET STABILIZATION

(75) Inventor: Stoffer Stienstra, Zyfflich (DE)

(73) Assignee: Quadrant Drug Delivery Ltd. (GB)

( * ) Notice: Subject to any disclaimer, the term of this patent is extended or adjusted under 35 U.S.C. 154(b) by 97 days.

(21) Appl. No.: 10/129,063

(22) PCT Filed: Oct. 23, 2000

(86) PCT No.: PCT/GB00/04078

§ 371 (c)(1),
(2), (4) Date: Apr. 30, 2002

(87) PCT Pub. No.: WO01/30141

PCT Pub. Date: May 3, 2001

(30) Foreign Application Priority Data

Nov. 12, 1999 (GB) ............................................... 9926838
May 22, 2000 (GB) ............................................... 0012372

(51) Int. Cl.$^7$ ................................................ A01N 1/02
(52) U.S. Cl. ........................................................ 435/2
(58) Field of Search ............................................. 435/2

(56) References Cited

U.S. PATENT DOCUMENTS 5,653,999 A    8/1997   Gaudreault et al.

FOREIGN PATENT DOCUMENTS

WO    WO 98/34478 A    8/1998

OTHER PUBLICATIONS

Nakano et al., "Retinol induces platelet aggregation via activation of phospholipase A2", BBRC 154 (3): 1075–80 (1988).*

Lewis, D.A. "Erythrocytes as microvasicles" retrieved from STN–International, Accession No. 121:212705 CA, XP002160827, abstract, 1992.

* cited by examiner

*Primary Examiner*—Sandra Saucier
(74) *Attorney, Agent, or Firm*—Saliwanchik, Lloyd & Saliwanchik

(57) ABSTRACT

A method for the production of stabilized platelets, comprises the steps of: (i) pre-activating platelets, to induce the formation of microvesicles; (ii) contacting the pre-activated platelets with a carbohydrate, whereby the carbohydrate is incorporated into the platelets; and (iii) drying the thus-loaded platelets.

5 Claims, No Drawings

PLATELET STABILIZATION

This application is a National Stage Application of International Application Number PCT/GB00/04078, published, pursuant to PCT Article 21(2).

FIELD OF THE INVENTION

This invention relates to methods for incorporating carbohydrates into platelets, to stabilise the platelets during storage.

BACKGROUND TO THE INVENTION

Blood platelets are one of the complex components involved in maintaining haemostasis. When the vessel wall is damaged, platelets adhere to exposed surfaces composed of collagen, microfibrils, and basement membrane. Adherent platelets promote the recruitment of other platelets to form an aggregated mass called a haemostatic platelet plug. The result is to activate coagulation proteins which provide the network to stabilize the platelet plug and reduce bleeding, allowing tissue repairs to occur.

Platelets are transfused to patients for many clinical indications. For instance, platelet infusions are used to correct deficiencies or dysfunctions of circulating platelets as a result of trauma, disease, or drug induced dysfunction. Patients suffering from idiopathic thrombocytopenia and those undergoing ablative chemotherapy are treated with platelet infusions. The increasing use of ablative chemotherapy for a wide variety of malignancies has resulted in an increased need for replacement platelet therapy.

A major difficulty in using isolated platelets is their short shelf-life. Platelets are only approved by the Food and Drug Administration (FDA) for storage in a liquid state for up to five days at room temperature, during which time the functional properties rapidly deteriorate. This causes many logistic problems in both civilian and military medicine.

Further drawbacks of storing platelets in a liquid state include the necessity of considerable storage space and constant agitation within bags of specially developed gas permeable plastics. Typically, single buffy-coat-derived platelets are stored in a suspending plasma volume of 45 to 65 ml. Recently, a study reported liquid storage establishing a minimum plasma volume of 30–50 ml (Home et al. (1994) Transfusion 34:39; and Ali et al. (1994) Transfusion 34:44). This storage method still requires considerable space, however, and the shelf life is not extended beyond approximately five days. The major problem with liquid storage is that the platelets need to be stored at approximately 20° C., as even short periods of exposure to lower temperatures during storage result in substantial changes in their in viva and in vitro properties (Moroff G. et al. (1994) Transfusion 34:317). As this storage usually also requires agitation of the platelets during storage at about 20° C. often in the presence of glucose, this presents optimal conditions for bacterial growth and this is a major problem with the storage of liquid platelets.

To minimise the problems of bacterial growth, refrigerated storage at 4° C. or frozen storage at −80° C. has been proposed. However, this requires methods to prevent the cold-activation of the platelets to be stored and the possible use of cryo-protectants. This method would however, require extensive washing of the platelets, to remove the cryo-protectants, before therapeutic use.

In addition, platelets are activated during the process of freeze drying and can only be used as a heamatology standard. The electrokinetic properties of the preserved platelets are different from those of fresh matched platelets. Other attempts at lyophilizing platelets have met with sub-optimal results. Fixing the platelet prior to freeze-drying improves their function, but these freeze-dried platelets need to be stored frozen at −80° C. (Read et al. (1995) Proc. Natl. Acad. Sci. 92:397).

WO-A-98/34478 discloses methods for stabilising platelets by incorporating the carbohydrate trehalose into the platelets, and then drying in the presence of a stabilising carbohydrate. The preferred method for incorporating the trehalose into the platelets is electropermeabilisation. Although this technique does result in high uptake of trehalose, the technique has the disadvantage of activating the platelets, and it can only be applied on a small scale unless expensive equipment is used.

SUMMARY OF THE INVENTION

The present invention is based on the realisation that platelets can be loaded with high concentrations of a carbohydrate sugar by pre-activating, but not fully activating, the platelets. Without wishing to be bound by theory, this may involve inducing the platelets to form microvesicles which incorporate carbohydrates on their formation, and then allowing uptake of the microvesicles by the platelets.

According to the present invention, a method for the production of stabilized platelets comprises the steps of:
(i) pre-activating platelets, to induce the formation of microvesicles;
(ii) contacting the pre-activated platelets with a carbohydrate, whereby the carbohydrate is incorporated into the platelets; and
(iii) drying the thus-loaded platelets.

The present invention provides a suitable method for, high efficient loading of platelets with a suitable carbohydrate, which can be carried out on a large scale and is sufficiently gentle to prevent activation of the platelets. After incorporation, the platelets may be dried by any suitable means, preferably in the presence of an external carbohydrate, for storage and transport.

DESCRIPTION OF THE INVENTION

The present invention is based at least in part on the realisation that microvesicle formation can be used to incorporate carbohydrates into platelets, without activating the platelets. Microvesicles are formed on the pre-activation of platelets, which is a well defined mechanism that has apparently been developed for the communication of signal molecules such as CD62p. Pre-activation (a term which will be understood by those of ordinary skill in the art) can be induced by many methods, including treating the platelets to induce pressure or stress, e.g. shear stress by, for example, filtration. Leukocyte reduction filters are appropriate for use to induce pressure or stress, e.g. shear stress by filtration. Centrifugation and other changes in the environment of the platelets may also be used to induce pre-activation.

Platelets may be obtained by any method known in the art. Typically, platelets are obtained by collecting blood into a suitable anticoagulant followed by obtaining platelet-rich plasma (PRP) by any method known in the art. After a platelet pellet is obtained by centrifugation, the pellet may be resuspended in a physiologically-acceptable solution, prior to pre-activation.

Typically, step (ii) of the method of the invention is carried out at a temperature of from 33° C. to 41° C. Step (i), i.e. pre-activation, may also be conducted at such a temperature.

The novel method can be carried out so that there is no further activation of the platelets. This may typically be carried out by conducting steps (i) and (ii) at least in the absence of calcium Dr in the presence of a calcium-chelating agents, e.g. EGTA or EDTA. However, the addition of such agents is not preferred for clinical use, and is not necessary if the pH of the platelets does not drop too far, e.g. below 6, such that activation occurs.

Preferably, the carbohydrate to be incorporated is a non-reducing sugar, for example sucrose, trehalose or raffinose. Typically, the carbohydrate will be present in the composition at a concentration of from 5 mM–80 mM, preferably 20 mM–60 mM and most preferably 40 mM–50 mM. More generally, the present method can be used to incorporate many different carbohydrates into platelets. The preferred carbohydrate used in the present invention is trehalose ($\alpha$-D-glucopyranosyl-$\alpha$-D-glucopyranoside).

After the carbohydrate has been incorporated into the platelets, the platelets may be resuspended in a drying buffer which typically contains a stabilising agent. The stabilising agent can be any carbohydrate that effects stabilisation of the dried platelets. Preferably the stabilising agent is trehalose. Drying the platelets may be carried out according to the description in WO-A-98/34478.

The following Example illustrates the invention.

EXAMPLE

Platelet-rich plasma (PRP) or platelet concentrate (PC), having a platelet concentration of approximately $1-3 \times 10^9$/ml, was washed twice with a buffer (100 mM NaCl, 10 mM KCl, 10 mM EGTA, 10 mM imidazole, pH 7.4) with centrifugation at 480 g. The pellet was resuspended in the buffer which also contains 30–50 mM trehalose. Pre-activation was induced by filtering the platelet concentrate, using a leukocyte reduction filter at 37° C.

After the filtering step, the platelets were incubated at 37° C. for up to 5 hours (optimal time was 2–3 hours). During this time, microvesicles formed during pre-activation were loaded with trehalose.

Platelet counts were then obtained. The platelets were pelleted (45 seconds at 14000 rpm) and the sugars were extracted using 80% methanol. The methanol was then evaporated with nitrogen/air, and the sugar samples redissolved in $H_2O$, prior to analysis. The amount of trehalose in the platelets was quantified using the anthrone reaction (Umbreit et al, Manometric and Biochemical Techniques 5th Edition, 1972) and by HPLC.

As a control experiment, the enzyme trehalase was added and the glucose concentration was measured after washing the cells. The original amount of trehalose in the cells was calculated and appeared to be similar to the quantity measured by HPLC.

What is claimed is:

1. A method for the production of stabilized platelets, comprising the steps of:
   (i) pre-activating platelets, to induce the formation of raicrovesicles;
   (ii) contacting the pre-activated platelets with a carbohydrate, whereby the carbohydrate is incorporated into the platelets thereby producing a carbohydrate loaded platelet; and
   (iii) drying the thus-loaded platelets;
   wherein step (i) comprises inducing shear stress on the platelets.

2. The method according to claim 1, wherein step (i) comprises filtering the platelets.

3. The method according to claim 1, wherein the carbohydrate is trehalose.

4. The method claim 1, wherein step (ii), and optionally also step (i), are carried out at a temperature of from 33° C. to 41° C.

5. The method according to claim 1, wherein step (ii) is conducted in the presence of a platelet activation inhibitor.

* * * * *

UNITED STATES PATENT AND TRADEMARK OFFICE
CERTIFICATE OF CORRECTION

PATENT NO. : 6,833,236 B1  Page 1 of 1
DATED : December 21, 2004
INVENTOR(S) : Stoffer Stienstra It is certified that error appears in the above-identified patent and that said Letters Patent is hereby corrected as shown below:

<u>Column 4,</u>
Line 21, "racirovesicles" should read -- microvesicles --.

Signed and Sealed this

Nineteenth Day of April, 2005

JON W. DUDAS
*Director of the United States Patent and Trademark Office*